US00PP09465P

United States Patent [19]

Challet

[11] Patent Number: Plant 9,465

[45] Date of Patent: Mar. 5, 1996

[54] CHRYSANTHEMUM PLANT NAMED 'CHAKARA'

[75] Inventor: Jean-Pierre Challet, Lafayette, Calif.

[73] Assignee: Selection New Plant Sarl, Le Cannet des Maures, France

[21] Appl. No.: 273,994

[22] Filed: Jul. 12, 1994

[51] Int. Cl.[6] ..... A01H 5/00

[52] U.S. Cl. ..... Plt./82.3

[58] Field of Search ..... Plt./82.3, 74.1, Plt./79, 76

[56] References Cited

U.S. PATENT DOCUMENTS

| | | | |
|---|---|---|---|
| P.P. 7,905 | 7/1992 | VandenBerg | Plt./79 |
| P.P. 7,931 | 8/1992 | van der Knaap | Plt./79 |
| P.P. 8,865 | 8/1994 | van der Jagt | Plt./82.3 |
| P.P. 8,869 | 8/1994 | van der Jagt | Plt./82.3 |

*Primary Examiner*—Howard J. Locker

*Attorney, Agent, or Firm*—Burns, Doane, Swecker & Mathis

[57] ABSTRACT

A new and distinct Chrysanthemum cultivar named 'Chakara' is provided. The new cultivar was the result of a controlled breeding program. Attractive bright bronze anemone blossoms are formed in profusion (as illustrated). The response period of the flowers is approximately eight weeks. Recurrent flower production throughout the year is possible. The plant possesses soft and thin stems, forms attractive leaves, and commonly assumes a height of approximately 30 to 35 cm. The new cultivar is particularly suited for use in the production of a decorative pot Chrysanthemum. No growth regulator is required to achieve the short plant height.

3 Drawing Sheets

SUMMARY OF THE INVENTION

The present invention comprises a new and distinct cultivar of Chrysanthemum, botanically known as *Dendranthema grandiflora,* and hereinafter is referred to by the cultivar name 'Chakara'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during October 1984 at Nuaille, Trementines, France. The female parent (i.e., the seed parent) was the 'Fada' cultivar (non-patented in the United States) having double flat purple blossoms that was created in France by a breeder named Bernard, and the male parent (i.e., the pollen parent) was the 'Domi' cultivar (non-patented in the United States) that is an old French cultivar having honey-colored blossoms in an anemone spray configuration. The parentage of the new cultivar can be summarized as follows:

'Fada'×'Domi'.

The seeds resulting from the above pollination were sown and many small plantlets were obtained which were physically and biologically different from each other. Selective study resulted in the identification of a single plant of the new variety.

It was found that the new cultivar of the present invention:

(a) exhibits in profusion attractive large bright bronze anemone blossoms, (b) exhibits a flower response period of approximately eight weeks, (c) is highly amenable to branching by pinching, (d) achieves a short plant height, and (e) is particularly suited for pot mum production on a recurrent basis throughout the year.

The new cultivar is intended primarily as a decorative pot anemone spray Chrysanthemum for growing indoors. However, the new cultivar can be grown outdoors at temperatures above freezing.

In the absence of debudding a profusion of blossoms form per stem (as illustrated). The new cultivar can also be grown as a disbud to form striking blooms. A greatly increased number of branches readily can be induced by pinching. The pinching of a cutting commonly produces 5 or more stems. No growth regulator is required to produce the short plant height.

The new cultivar can be considered to be an October-flowering greenhouse variety with the natural flowering season commonly occurring in weeks 41 and 42 of the year. Attractive blossoms can be produced on a recurrent basis throughout the year with the indicated eight week response period. The blossoms commonly last at least one and one-half weeks on the plant, and commonly less than one week when placed in a vase.

Asexual reproduction of the new cultivar by cuttings initially taken during 1985, as performed in Nuaille, Trementines, France, in a controlled environment has demonstrated that the characteristics of the new cultivar as herein described are firmly fixed and are retained through successive generations of asexual propagation.

'Chakara' has not been observed under all possible environmental conditions to date. Accordingly, it is possible that the phenotype may vary somewhat with variations in the environment, such as temperature, light, day length, contact with pesticides and/or subjection to growth retardant treatments.

The 'Chakara' cultivar can be readily distinguished from the 'Chakuse' cultivar (copending U.S. Plant patent application Ser. No. 08/273,993, filed Jul. 12, 1994) that was produced by the cross of the same parent cultivars. More specifically, the new 'Chakara' cultivar exhibits a bright bronze anemone capitulum and the 'Chakuse' cultivar exhibits a yellow spider capitulum, the 'Chakara' cultivar exhibits a normal growth habit unlike the bushy growth habit of the 'Chakuse' cultivar, the 'Chakara' cultivar exhibits ray florets having denated tips while those of 'Chakuse' are round, the 'Chakara' cultivar exhibits petaloid disc florets while those of the 'Chakuse' cultivar are tubular, and the 'Chakara' cultivar exhibits a response period of approximately eight weeks and the 'Chakuse' cultivar exhibits a longer response period of approximately eight and one-half weeks.

Mutations of the 'Chakara' cultivar are the 'Chaplou' cultivar (copending U.S. Plant patent application Ser. No. 08/273,992, filed Jul. 12, 1994) and the 'Chaprial' cultivar (copending U.S. Plant patent application Ser. No. 08/274,001, filed Jul. 12, 1994). Each of these additional cultivars can be readily distinguished from the parent 'Chakara' cultivar with respect to a number of plant characteristics.

For instance, the 'Chaplou' cultivar exhibits a red bronze capitulum unlike the bright bronze capitulum of the 'Chakara' cultivar, a stem coloration of Yellow-Green Group 146D instead of Yellow-Green 144A for the 'Chakara' cultivar, anthocyanin coloration mainly at the nodes unlike the 'Chakara' cultivar, an angular stem cross section unlike the round stem cross section of the 'Chakara' cultivar, medium leaf serration unlike the medium to coarse leaf serration of the 'Chakara' cultivar, an upper leaf surface coloration of Yellow-Green Group 144A but more green unlike the coloration of Green Group 137B to 137C for the 'Chakara' cultivar, the absence of a claw in the base of the sinus between lateral leaf lobes unlike the 'Chakara' cultivar, a mucronate leaf apex unlike the cuspidate leaf apex of the 'Chakara' variety, a concave ray floret cross section unlike the generally flat ray floret cross section of the 'Chakara' cultivar, and a long day leaf count of approximately 15 to 19 unlike the 17 to 22 count commonly exhibited by the 'Chakara' cultivar.

The 'Chaprila' cultivar exhibits a bright golden yellow capitulum unlike the bright bronze capitulum of the 'Chakara' cultivar, a stem coloration of Yellow-Green Group 146C instead of Yellow-Green Group 144A for the 'Chakara' cultivar, anthocyanin coloration only at ribs unlike the 'Chakara' cultivar, an angular stem cross section unlike the round stem cross section of the 'Chakara' cultivar, generally less coarseness in the leaf serration than the 'Chakara' cultivar, generally a lighter leaf coloration than the 'Chakara' cultivar, generally parallel margins of the sinus between lateral leaf lobes unlike the converging margins of the 'Chakara' cultivar, a mucronate leaf apex unlike the cuspidate leaf apex of the 'Chakara' variety, a weakly convex ray floret cross section unlike the generally flat ray floret cross section of the 'Chakara' cultivar, and a long day leaf count of approximately 17 to 19 as compared to a count of approximately 17 to 22 for the 'Chakara' cultivar.

The new 'Chakara' cultivar of the present invention is being marketed under the Mercury trademark.

BRIEF DESCRIPTION OF THE PHOTOGRAPHS

The accompanying photographs were prepared during June, 1994, and show as nearly true as it is reasonably possible to make the same in color illustrations of this character, typical plants and plant parts of the new cultivar of the present invention. The plants were 13 weeks of age and were grown at Nuaille, Trementines, France, under standard greenhouse conditions which approximate those commonly utilized for the production of decorative pot mums. The plants had been pinched once and had not been dibudded. No growth regulant was utilized. Any labels shown in the photographs are 2.5 cm. in width and can be used for size comparisons.

DETAILED DESCRIPTION

Figure 1:
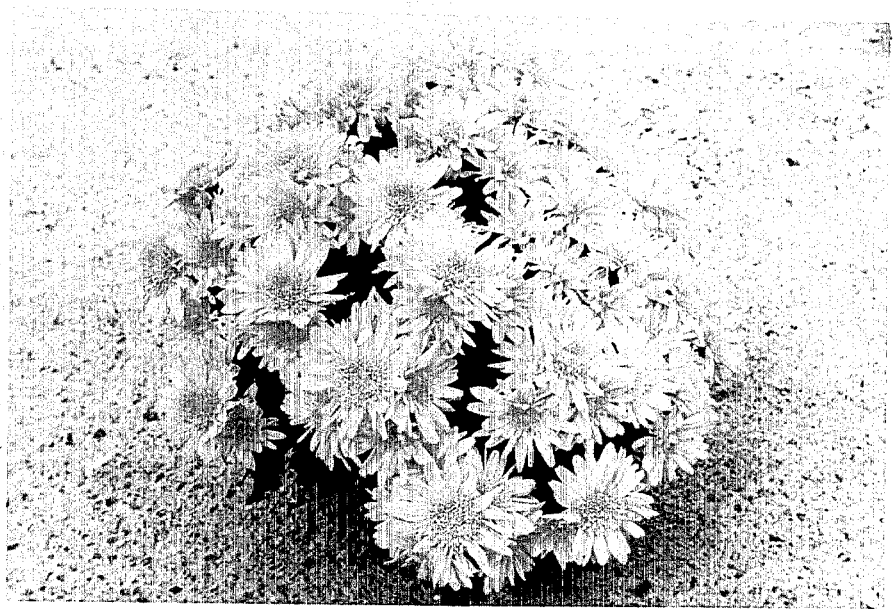
FIG. 1 illustrates typical specimens of the overall plant wherein three cuttings were placed in a 20 cm. pot. The bright bronze anemone flowers, as well as the foliage, are apparent.
Figure 2:
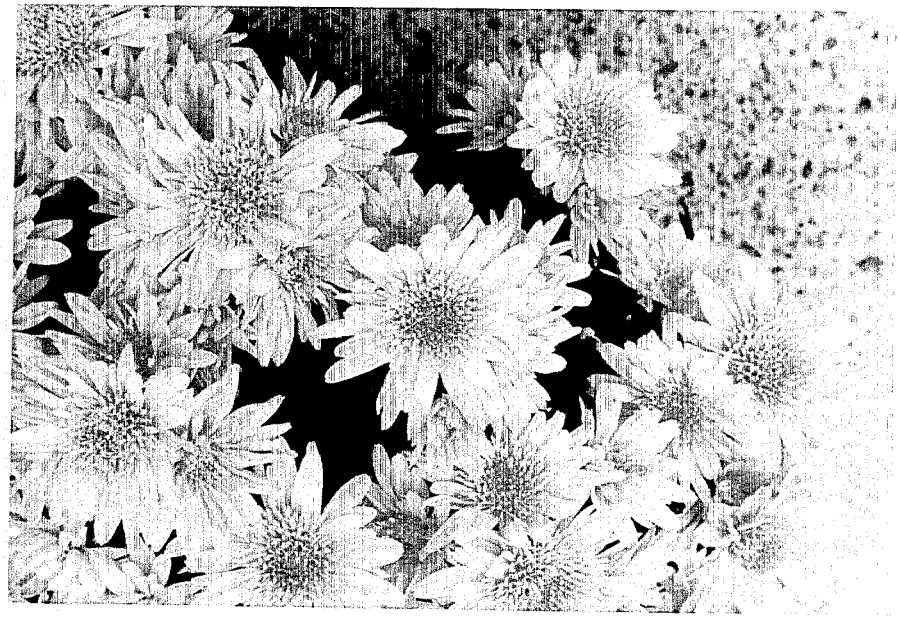
FIG. 2 illustrates a closer view of typical flowers in various stages of opening. It is apparent that the blossom coloration tends to fade as the blossoms mature.
Figure 3:
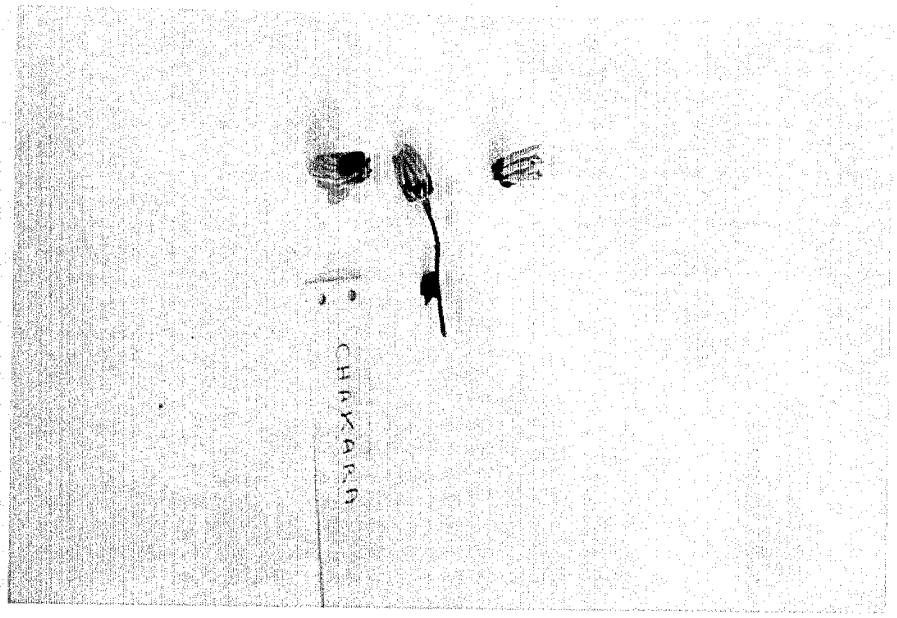
FIG. 3 illustrates from left to right, under, side, and upper views of largely unopened buds.
Figure 4:
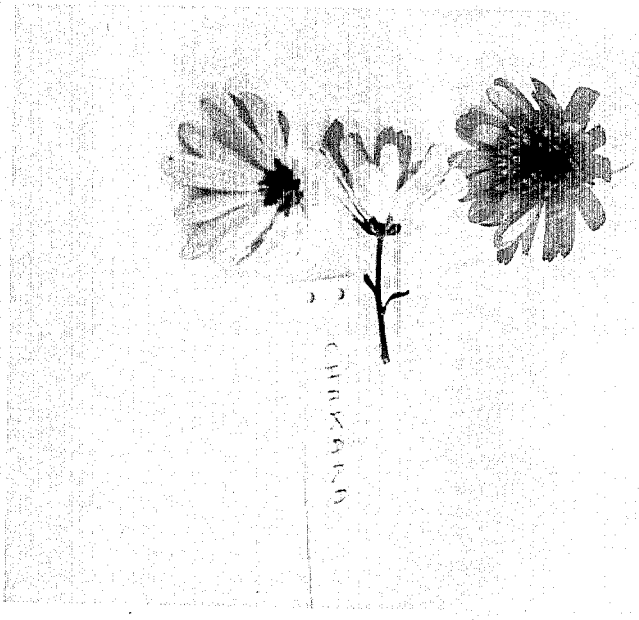
FIG. 4 illustrates from top to right, under, side, and upper views of the flowers in the course of opening. The darker coloration of the upper surfaces of the blossoms when immature is visible.
Figure 5:
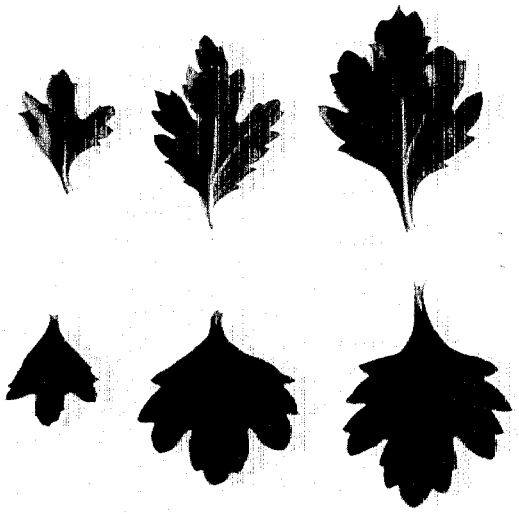
FIG. 5 illustrates at the top row the under surfaces of typical leaves of various sizes and at the bottom row the upper surfaces of typical leaves of various sizes.

The chart used in the identification of colors described hereafter is the R.H.S. Colour Chart of the Royal Horticultural Society, London, England. In some instances more common color terms are provided and are to be accorded their usual dictionary significance. The plants described were 13 weeks of age and were grown at Nuaille, Trementines, France, under standard greenhouse conditions which approximate those commonly utilized for the production of decorative pot mums.

Classification:

*Botanical.*—*Dendranthema grandiflora,* cv. 'Chakara'.

*Commercial.*—Decorative pot mum.

INFLORESCENCE

A. Capitulum:

*Type.*—Anemone.

*Diameter across face.*—Medium, approximately 8 to 10 cm. on average when fully expanded.

*Frequency.*—Corymbiform, and blossoms form in profusion (as illustrated).

B. Corolla of ray and disc florets:

*Disc florets.*—Petaloid, numerous, very long, massed and clearly visible at all stages of flower head development, and commonly form a disc of approximately 4 to 5 cm. in diameter.

*General tonality.*—Bright bronze capitulum that tends to fade somewhat as the blossoms fully mature.

*Color of disc florets.*—Before dehiscence, Greyed-Orange Group 169B commonly with some coloration of Yellow-Orange Group 15A at the extreme tip. After dehiscence, the tube commonly is between Yellow-Orange Group 17D and Yellow-Orange Group 23C, and the throat commonly is Yellow-Orange Group 15B tinged with Orange-Red Group 34A, and commonly tipped with yellow coloration.

*Color ray florets.*—On the outermost florets, Yellow-Orange Group 16C and lightly tinged with Orange-Red Group 34A with the deeper coloration appearing towards the tip. On the innermost florets, Yellow Group 13B, and lightly overlaid with Orange-Red Group 34A thereby providing a general tonality of Greyed-Orange Group 169B with deeper coloration commonly being present towards the tip. The coloration tends to fade (as illustrated) as the blossoms mature with the fading commonly beginning at the tips of the florets.

*Configuration ray florets.*—Flat in cross section, rough in texture, generally straight, medium to high length to width ratio, and possess dentated tips.

C. Reproductive organs:

*Androecium.*—Generally present with disc florets and absent in ray florets.

*Gynoecium.*—Generally present with most disc florets and with most ray florets.

*Pollen.*—Generally present in a substantial quantity, and golden-yellow in coloration.

*Fragrance.*—Typical of Chrysanthemum.

PLANT

A. General appearance:

*Height.*—Short, and approximately 30 to 35 cm. in height on average at 10 weeks of age.

*Growth habit.*—Normal.

B. Foliage:

*Color (upper surface).*—Green Group 137B to 137C.

*Color (under surface).*—Generally lighter green, approaches Green Group 138A.

*Long day leaf count.*—Approximately 17 to 22 leaves per typical stem in a long day crop before the bud occurs.

*Configuration.*—Very short to short and lobed (as illustrated).

*Texture.*—Fleshy.

*Serration.*—Medium to coarse.

*Shape of base.*—Asymmetric and tending to be obtuse.

*Apex.*—Cuspidate.

*Internode length.*—Very short to short.

*Stems.*—Thin, soft, round in cross section, nearest to Yellow-Green Group 144A in coloration, and commonly with anthocyanin coloration.

*Claw in base of sinus between lateral lobes.*—Present.

*Margins of sinus between lateral lobes.*—Converging.

I claim:

1. A new and distinct cultivar of Chrysanthemum plant named 'Chakara', substantially as herein shown and described, which (a) exhibits in profusion attractive large bright bronze anemone blossoms, (b) exhibits a flower response period of approximately eight weeks, (c) is highly amenable to branching by pinching, (d) achieves a short plant height, and (e) is particularly suited for pot mum production on a recurrent basis throughout the year.

* * * * *